(12) United States Patent
Van Noy (10) Patent No.: US 9,186,243 B2
(45) Date of Patent: Nov. 17, 2015

(54) ACCOMMODATIVE INTRAOCULAR LENS AND METHOD OF IMPLANTATION

(75) Inventor: Stephen J. Van Noy, Southlake, TX (US)

(73) Assignee: NOVARTIS AG, Basel (CH)

( * ) Notice: Subject to any disclaimer, the term of this patent is extended or adjusted under 35 U.S.C. 154(b) by 3 days.

(21) Appl. No.: 13/476,631

(22) Filed: May 21, 2012

(65) Prior Publication Data

US 2012/0310343 A1 Dec. 6, 2012

Related U.S. Application Data

(60) Provisional application No. 61/491,819, filed on May 31, 2011.

(51) Int. Cl.
*A61F 2/16* (2006.01)

(52) U.S. Cl.
CPC ............. *A61F 2/1635* (2013.01); *A61F 2/1624* (2013.01); *A61F 2250/0003* (2013.01); *A61F 2250/0051* (2013.01)

(58) Field of Classification Search
CPC .............................. A61F 2/1624; A61F 2/1635
USPC ............. 623/6.13, 6.37, 6.38, 6.39, 6.4, 6.41, 623/6.51, 6.62, 6.59, 6.43, 6.16
See application file for complete search history.

(56) References Cited

U.S. PATENT DOCUMENTS

| | | | |
|---|---|---|---|
| 4,888,012 A * | 12/1989 | Horn et al. | 623/6.13 |
| 5,035,710 A | 7/1991 | Nakada et al. | |
| 5,171,318 A * | 12/1992 | Gibson et al. | 623/5.16 |
| 5,213,579 A | 5/1993 | Yamada et al. | |
| 6,063,116 A * | 5/2000 | Kelleher | 623/6.56 |
| 6,063,396 A | 5/2000 | Kelleher | |
| 6,228,114 B1 * | 5/2001 | Lee | 623/5.12 |
| 2003/0149480 A1 | 8/2003 | Shadduck | |
| 2005/0107873 A1 * | 5/2005 | Zhou | 623/6.13 |
| 2006/0212116 A1 | 9/2006 | Woods | |
| 2007/0021831 A1 * | 1/2007 | Clarke | 623/6.13 |
| 2008/0077239 A1 | 3/2008 | Zickler et al. | |
| 2009/0312836 A1 | 12/2009 | Pinchuk et al. | |
| 2009/0319040 A1 | 12/2009 | Khoury | |

(Continued)

FOREIGN PATENT DOCUMENTS

| WO | 2005057272 A2 | 6/2005 |
|---|---|---|
| WO | 2008036674 A1 | 3/2008 |

(Continued)

OTHER PUBLICATIONS

International Preliminary Report on Patentability; PCT/US2012/038973; Dec. 2013.
International Search Report and Written Opinion; PCT/US2012/038973; Oct. 2012.

(Continued)

*Primary Examiner* — David H Willse
*Assistant Examiner* — Javier Blanco
(74) *Attorney, Agent, or Firm* — Jason Finch (57) ABSTRACT

An accommodating intraocular lens (AIOL) adapted for implantation into a capsular bag includes an outer shell, a valve, and a force transfer assembly. The outer shell includes at least one surface modification on at least a periphery of the outer shell to promote bonding with the capsular bag. The valve is configured to permit injection of a fill material. The force transfer assembly in the outer shell is adapted to transfer forces from the capsular bag to change the shape of the filled outer shell in response to changes in capsular bag shape.

4 Claims, 7 Drawing Sheets

(56) References Cited

U.S. PATENT DOCUMENTS

| | | | |
|---|---|---|---|
| 2010/0016963 A1* | 1/2010 | Park | 623/6.32 |
| 2010/0131058 A1* | 5/2010 | Shadduck | 623/6.13 |
| 2010/0324671 A1 | 12/2010 | Shadduck | |
| 2010/0324674 A1 | 12/2010 | Brown | |
| 2011/0130831 A1* | 6/2011 | Badawi et al. | 623/6.14 |
| 2012/0191185 A1* | 7/2012 | Colvin et al. | 623/6.62 |
| 2012/0303118 A1* | 11/2012 | DeBoer et al. | 623/6.13 |

FOREIGN PATENT DOCUMENTS

| | | |
|---|---|---|
| WO | 2008108525 A1 | 9/2008 |
| WO | WO 2009021327 A1 * | 2/2009 |

OTHER PUBLICATIONS

EP12792183.1;Supplementary Partial European Search Report; European Patent Office, Nov. 20, 2014, 7 pgs.

* cited by examiner

ACCOMMODATIVE INTRAOCULAR LENS AND METHOD OF IMPLANTATION

RELATED APPLICATIONS

This application claims priority to U.S. provisional application Ser. No. 61/491,819, filed on May 31, 2011, the contents which are incorporated herein by reference.

FIELD OF THE INVENTION

This invention relates generally to the field of intraocular lenses (IOL) and, more particularly, to accommodative IOLs.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens. The lens is held in place within the posterior chamber of the eye by a membrane known as the capsular bag or posterior capsule, immersed in the aqueous humor. The shape of the lens and the refractive index of the lens relative to the aqueous humor determine where light rays are focused onto the retina.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL). Cataractous lenses are often removed by a surgical technique called phacoemulsification. During this procedure, an opening is made in the anterior side of the capsular bag, a thin membrane enclosing the natural lens. A thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

In the natural lens, multifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can be focused alternatively on near and far objects. As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

When a cataract or other disease requires the removal of the natural lens and replacement with an artificial intraocular lens ("IOL"), the IOL used to replace the natural lens has often been a monofocal lens. These lenses do not change power in response to the movement of the capsular bag, requiring that the patient use a pair of spectacles or contact lenses for near vision. However, there are several examples in the prior art of bladder or bag-like intraocular lenses that consist of an outer flexible skin filled with a viscous gel. The resulting lens completely fills the capsular bag and is very soft and pliable, much like the natural lens. See for example, U.S. Pat. No. 4,373,218 (Schachar), U.S. Pat. No. 4,585,457 (Kalb), U.S. Pat. No. 4,685,921 (Peyman), U.S. Pat. No. 4,693,717 (Michelson), U.S. Pat. No. 5,275,623 (Sarfarazi), U.S. Pat. No. 4,822,360 (Deacon), U.S. Pat. No. 5,489,302 (Skottun) and U.S. Pat. No. 6,217,612 (Woods). But in order to provide accommodation, movement of the ciliary muscle must be adequately transmitted to the lens system through the capsular bag, and none of these references disclose a mechanism for ensuring that there is a tight connection or fixation between the capsular bag and the lens system.

Therefore, a need continues to exist for a safe and stable accommodative intraocular lens system and method for implantation that provides accommodation over a broad and useful range.

BRIEF SUMMARY OF THE INVENTION

An accommodating intraocular lens (AIOL) adapted for implantation into a capsular bag includes an outer shell, a valve, and a force transfer assembly. The outer shell includes at least one surface modification on at least a periphery of the outer shell to promote bonding with the capsular bag. The valve is configured to permit injection of a fill material. The force transfer assembly in the outer shell is adapted to transfer forces from the capsular bag to change the shape of the filled outer shell in response to changes in capsular bag shape.

DETAILED DESCRIPTION OF THE INVENTION

Various embodiments of the present invention may provide an improved accommodating lens by promoting adhesion of the capsular bag around mechanical features of the accommodating IOL. This provides a more robust mechanical connection between the bag and the IOL to allow the flattening and relaxing of the bag, as opposed to the force of the ciliary muscles, to move the lens. The changes in shape of the capsular bag are in turn used either to deform the lens to produce a power change (akin to the accommodation of the natural lens) or to produce a change in IOL power by separating two optical elements.

Various embodiments of the present invention also include mechanical structures for translating the force produced by movement of the capsular bag into forces producing either deformation of the lens or separation of optical elements of the lens. By combining this with strong adhesion of the capsular bag to the IOL at particular points along the mechanical structure, particular embodiments of IOLs according to the present invention advantageously provide increased mechanical efficiency and a greater degree of accommodative change in the optical power of the IOL.

Figure 1:
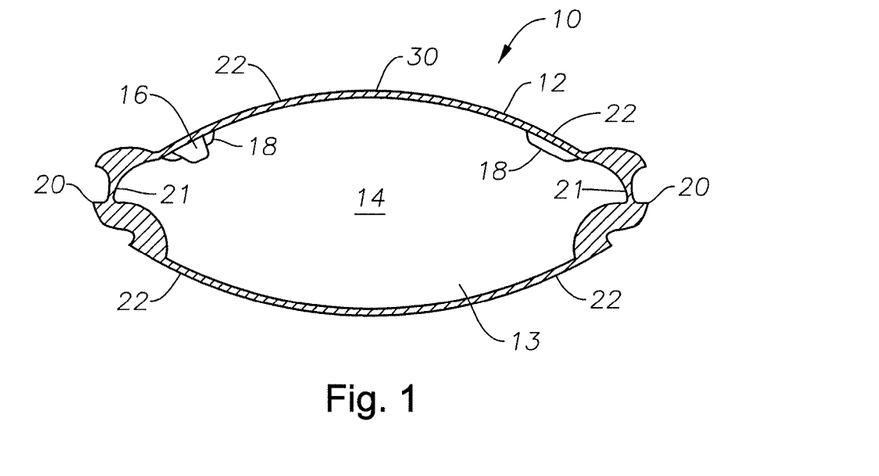
FIG. 1 is an enlarged cross-sectional view of the lens according to a particular embodiment of the present invention.

As best seen in FIG. 1, a lens 10 according to a particular embodiment of the present invention generally consists of an outer shell 12 defining internal void 13 which contains and interior fill material 14. The outer shell 12 is preferably formed in any suitable overall diameter or length, for example, around 10 millimeters, for implantation in the capsular bag of the eye. The outer shell 12 preferably is made from a soft, foldable material that is inherently resistant to the formation of posterior capsular opacification ("PCO"), such as a soft acrylic. In certain embodiments, the material of the outer shell 12 may be relatively more elastic than the capsular bag, so that outer shell 12 can be moved by the capsular bag with relative ease. The outer shell 12 contains a fill valve 16 allowing fill material 14 to be injected into or removed from void 13.

The outer shell 12 may also include a force transfer structure, such as a plurality of stiffening radial ribs 18 having an appropriate spacing, e.g., 30°, and/or may be attached to a peripheral band surrounding the lens 10 (as described in greater detail below). In the depicted embodiment, the lens 10 also includes living hinges 21 at the periphery, so as to facilitate the shape change of the surfaces. In particular embodiments, a peripheral band may be coupled to the living hinge assembly to transfer forces from the capsular bag into actuation of the living hinges. The outer shell 12 may also contain sharp peripheral corners 20 designed to prevent equatorial cell proliferation on the optical surfaces of the lens 10, but cell adhesion is preferably encouraged around the hinges 21 at the periphery of the lens to improve the mechanical efficiency of force transfer between the capsular bag and lens 10.

At least part of the outer shell 12 is coated with surface modification 22, which may include coatings, texturing, or other suitable variation designed to promote protein adhesion. Examples of such coatings include complementary proteins, growth factors for the capsular bag, chitin or other organic chemicals used in signaling cell growth conditions. The polymer structure used to form lens 10 may be protein-fortified, so that the lens material itself has a surface that encouraged protein bonding. Other suitable surface modifications include nano-channels or other structures allowing cellular interpenetration into the lens structure. Such structures may also include coatings or treatments to promote cell growth and binding within the interpenetrating cell/lens network. Still other suitable surface modifications include the use of biocompatible adhesives.

Figure 2:
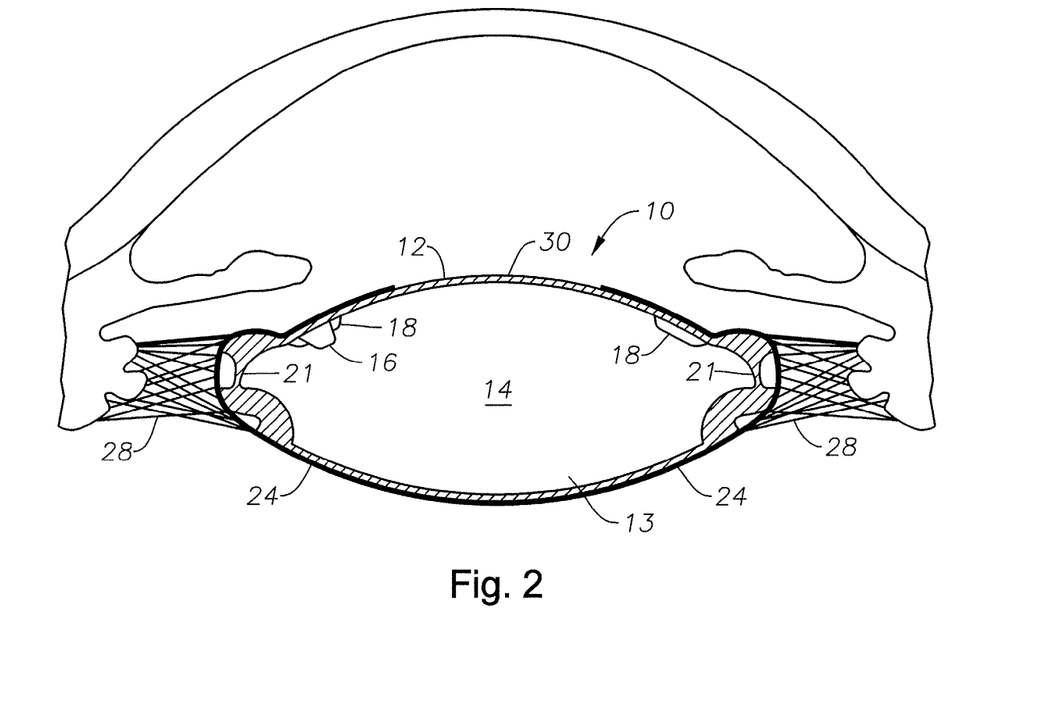
FIG. 2 is an enlarged cross-sectional view of the lens of FIG. 1 showing the lens implanted in a capsular bag.
Figure 3:
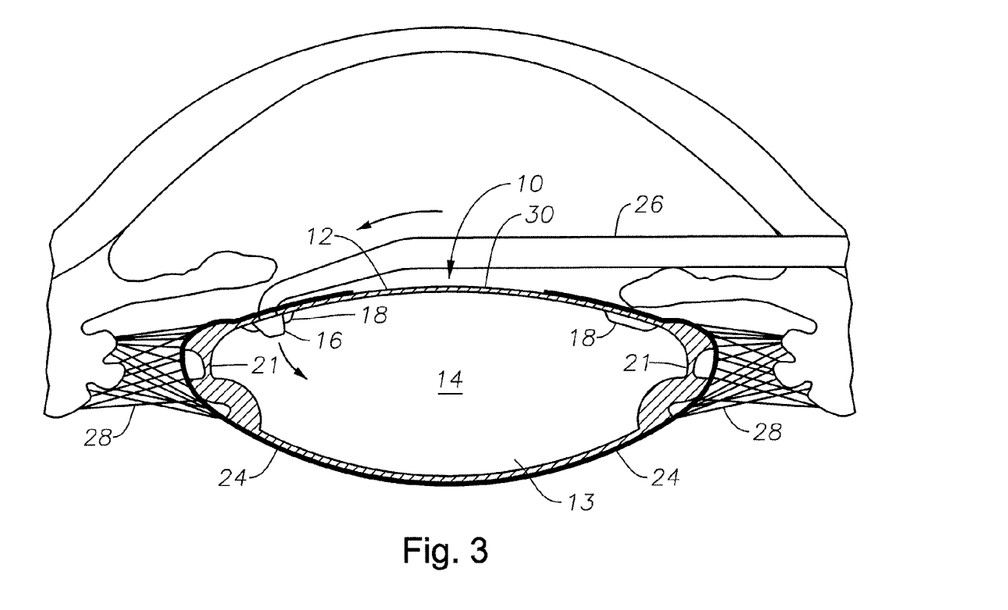
FIG. 3 is an enlarged cross-sectional view of the lens of FIG. 1 showing the lens implanted in a capsular bag and material being injected into the lens to approximate the unaccommodated state.

Fill material 14 preferably is a liquid, gel, or low molecular weight polymer with a refractive index greater than that of the surrounding aqueous humor. Such materials may include (but are not limited to) silicone oil, perfluoron, and cross-linked or non-cross-linked polymer gels. It is also preferable to minimize losses of fill material 14 due to diffusion, so outer shell 12 should preferably be relatively impermeable to fill material 14 and the surrounding aqueous humor. As best seen in FIG. 2, lens 10 may be implanted in capsular bag 24 in an unfilled state. As seen in FIG. 3, internal void 13 is then filled with fill material 14 through valve 16 using an appropriate instrument, such as cannula 26 so that lens 10 approximates the shape of the natural lens in a disaccommodated state, which results in anterior surface 30 of outer shell 12 being relatively flat. In the depicted embodiment of FIG. 2, the anterior surface 30 changes shape considerably during accommodation while the posterior surface remains relatively unchanged in shape, but alternative embodiments could have both the anterior and the posterior surfaces changing shape to a lesser or greater degree. One advantage of thickening the posterior surface or making the posterior surface relatively more rigid is that the posterior surface could be relatively fixed in order to more easily allow aspheric and/or toric correction to be used in lens 10. Diffractive and/or multifocal optics could be incorporated into the surface as well.

Figure 4:
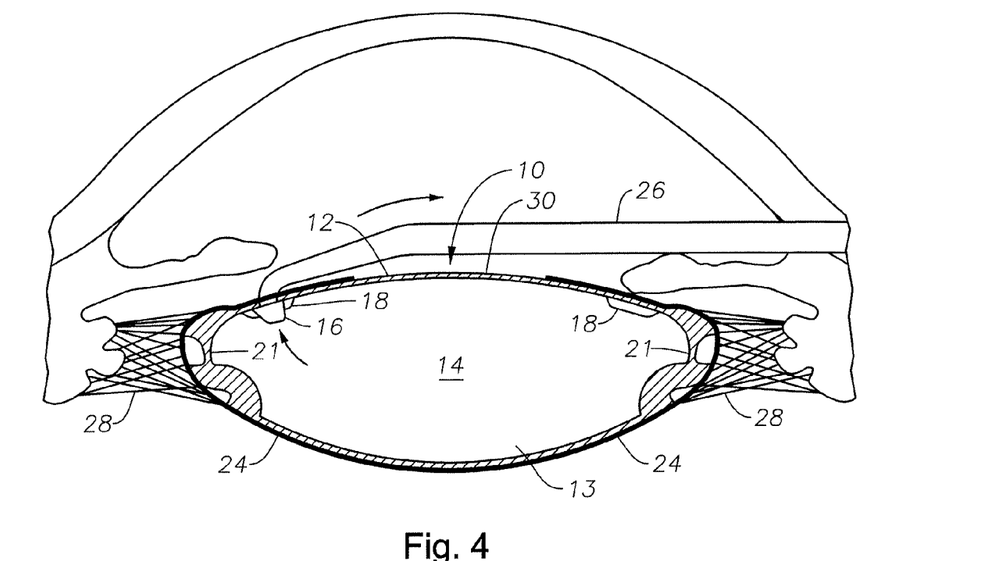
FIG. 4 is an enlarged cross-sectional view of the lens of FIG. 1 showing the lens implanted in a capsular bag and material being removed from the lens.
Figure 5:
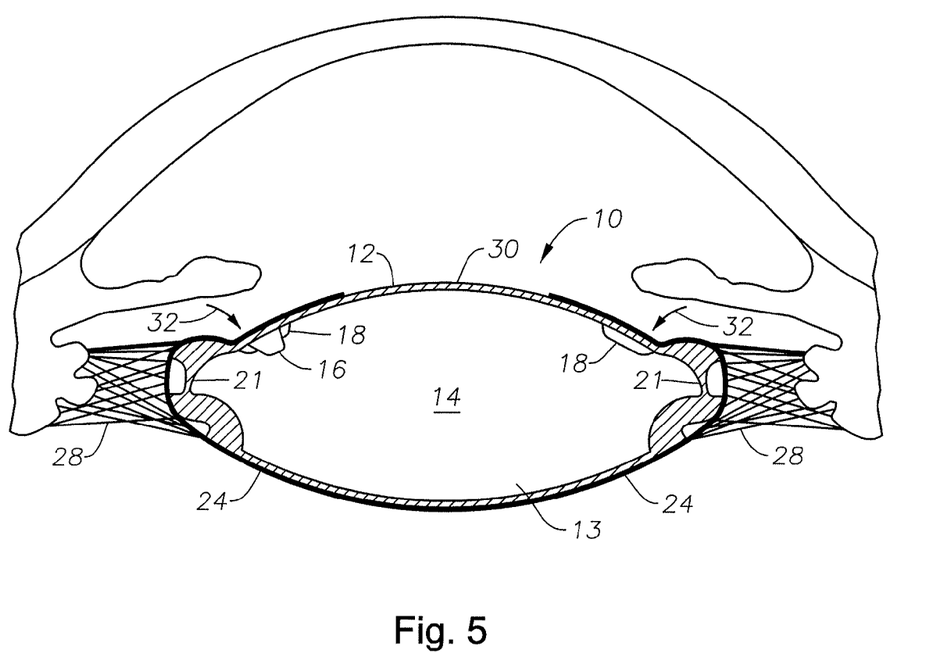
FIG. 5 is an enlarged cross-sectional view of the lens of FIG. 1 showing the lens implanted in a capsular bag and being in the accommodated state.

When lens 10 is over-filled, zonules 28 are in a relaxed position. Lens 10 is left in this over-filled condition for a period of time sufficient for protein adhesions to form between outer shell 12 and capsular bag 24, e.g., 2-4 weeks. As best seen in FIG. 4, after protein adhesions have formed between outer shell 12 and capsular bag 24, sufficient filler material 14 is removed from void 13 through valve 16 for lens 10 to adopt the shape of a disaccommodated lens, as best seen in FIG. 5, with zonules 28 in tension and anterior surface 30 having a more rounded shape relative to the overfilled state, as shown by arrows 32. The lens 10 may be also mechanically biased toward the accommodated state, so that when the capsular bag relaxes, the default tendency of the lens 10 is to restore to the accommodated state. For example, the living hinges 21 may have a spring action that tends to urge the anterior surface of the lens 30 into the accommodated shape.

Figure 6:
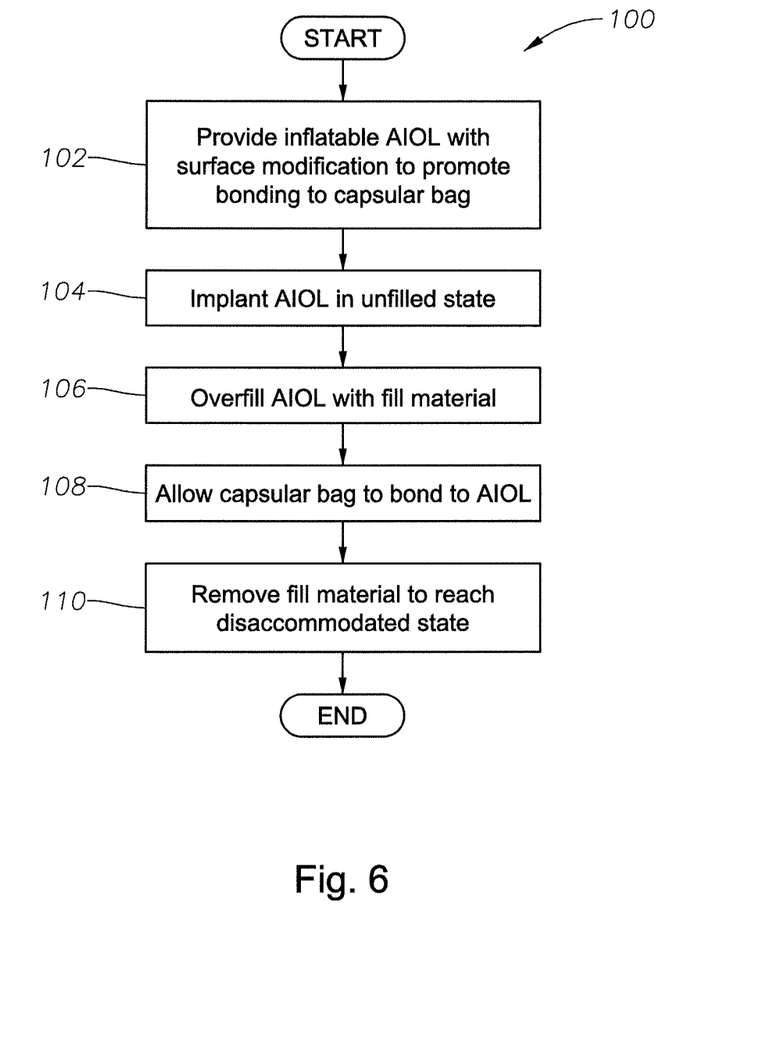
FIG. 6 is flowchart showing a method of implanting an inflatable accommodating lens according to particular embodiments of the present invention.

FIG. 6 is a flowchart 100 showing an example implantation method according to particular embodiments of the present invention. At step 102, an inflatable accommodating lens ("AIOL") is provided with a surface modification to promote protein adhesion with the capsular bag. At step 104, the AIOL is implanted in an unfilled state. At step 106, the AIOL is overfilled to facilitate contact with the capsular bag. At step 109, the capsular bag is allowed to heal around the AIOL for sufficient time to allow bonding between the capsular bag and the AIOL. At step 110, fill material is removed from the AIOL to reach a disaccommodated state for the AIOL.

Figure 7:
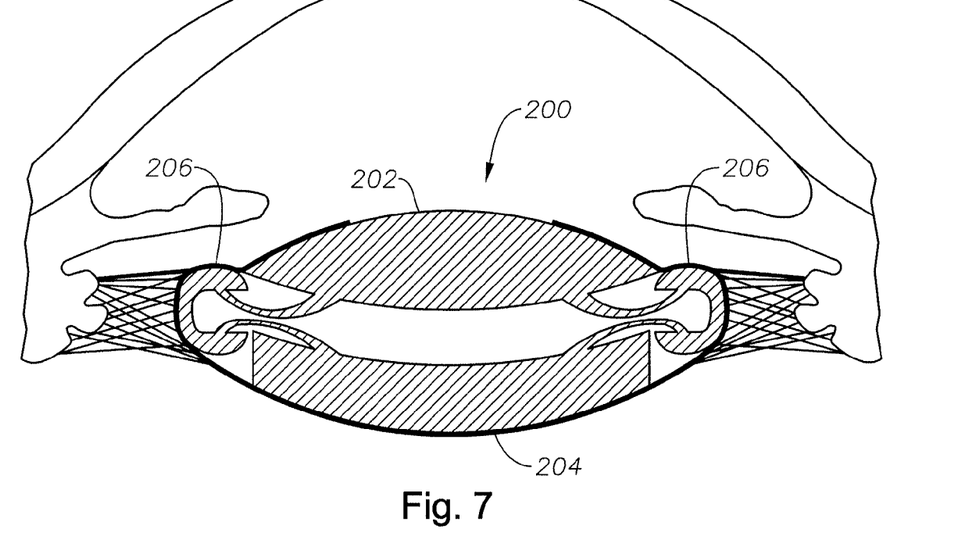
FIG. 7 illustrates a dual-optic accommodating IOL according to a particular embodiment of the present invention.

FIG. 7 is a cross sectional view of a dual-optic AIOL 200 according to another embodiment of the present invention. For purposes of this specification, "dual-optic" refers to an AIOL including at least two optical elements, but such a dual-optic AIOL could include additional optical elements as well. The dual-optic AIOL 200 includes an anterior optical element 202 and a posterior optical element 204. Preferably, one of the anterior optical element 202 or posterior optical element 204 has a positive power, and the other has a negative power so that the difference between the powers is relatively large and a change in spacing between the optical elements 202 and 204 produces a significant change in overall optical power. One or both surfaces may also include aspheric, toric, diffractive, and/or multifocal correction as well. While both optical elements 202 and 204 are shown within the capsular bag, the AIOL 200 could include a sulcus-fixated anterior optical element 202.

The AIOL 200 also includes interlocking features 206 between the optical elements 202 and 204. Interlocking features 206 are located peripherally around the optical elements 202 and 204, and the interlocking features 206 also include surface modifications, such as the ones described above, to promote bonding of the capsular bag to the interlocking features 206. Interlocking features 206 may be formed integrally, so that the entire AIOL 200 is a single piece, or they can alternatively be complementary features attached to their respective optical elements 202 and 204 so that the interlocking features 206 are connected to one another before or during implantation. While the interlocking features 206 are illustrated in an integrated living hinge configuration, other arrangements could function suitably as well, including arrangements using a hook-and-clasp or hinge pin. In the illustrated embodiment, the interlocking features 206 are configured to hold the optical elements 202 and 204 spaced apart from one another in the disaccommodated state to prevent adhesion.

Because the capsular bag is firmly attached to the interlocking features 206, the capsular bag pulls the interlocking features 206 outwardly when flattened. The interlocking features 206 are shaped such that the optical elements 202 and 204 are pulled together when the interlocking features 206 are pulled outward. The interlocking features 206 are also shaped to store mechanical energy when the optical elements 202 and 204 are pulled together. For example, the interlocking features 206 may include spring windings that are twisted by pulling outwardly on the interlocking features 206. Thus, when the capsular bag is flattened, the AIOL 200 will be pulled into a disaccommodated (lower power) state. When the capsular bag relaxes, the interlocking features 206 release the stored mechanical energy to force the optical elements 202 and 204 apart, increasing the optical power of the AIOL 200 to provide accommodation.

In order for the capsular bag to have adequate tension to pull the interlocking features 206, the capsular bag should be bonded firmly to the interlocking features 206 in the disaccommodated state. To facilitate this bonding, the AIOL 200 may include retaining features, such as clips, that hold the optical elements 202 and 204 in the disaccommodated state with mechanical energy being stored in the interlocking features 206. The retaining features may be left in place for two or more weeks while postsurgical healing and bonding of the capsular bag is taking place. Following the bonding process, the retaining features can be removed or otherwise disabled, such as by directing laser pulses to sever the retaining features. The retaining features could also be made biodegradable, so that they would erode over time and eventually dissolve after the capsular bag was well-bonded. Once the retaining features are no longer holding the optical elements 202 and 204 together, the mechanical energy stored in spring members can be released when the tension on the capsular bag is released, providing accommodation as described above.

Figure 8A:
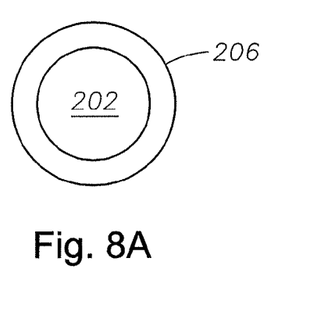
FIGS. 8A, 8B, and 8C illustrates various embodiments of a dual-optic AIOL according to particular embodiments of the present invention as viewed along the optical axis.
Figure 8B:
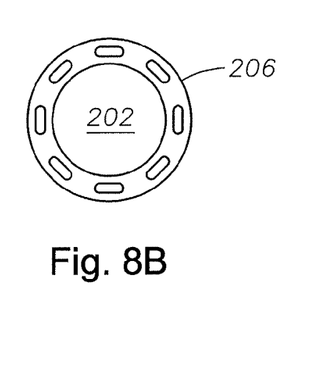
Figure 8C:
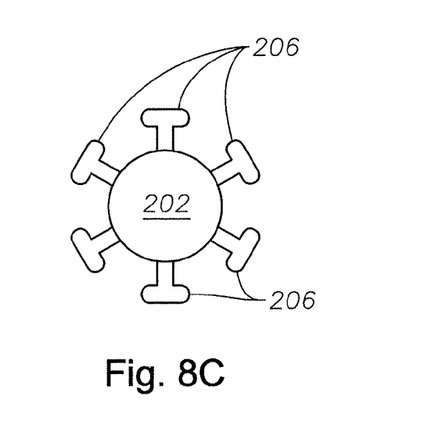

FIGS. 8A, 8B, and 8C illustrate several different embodiments of interlocking features 206 as viewed along the optical axis. In the embodiment shown in FIG. 8A, the interlocking features 206 form a continuous circle with surface modification at the periphery of the AIOL 200 to facilitate attachment to the capsular bag. In the embodiment shown in FIG. 8B, the interlocking features 206 include fenestrations to facilitate interpenetration of capsular cells into the interlocking features 206. In the embodiment shown in FIG. 8C, the interlocking features 206 are joined at six T-shaped junctions that have surface modifications to promote capsular cell growth and bonding to the interlocking features 206. The illustrated embodiments are only examples, and any structure capable of storing mechanical energy that has appropriate surface modifications to promote bonding with the capsular bag can be suitable for interlocking features 206.

Figure 9:
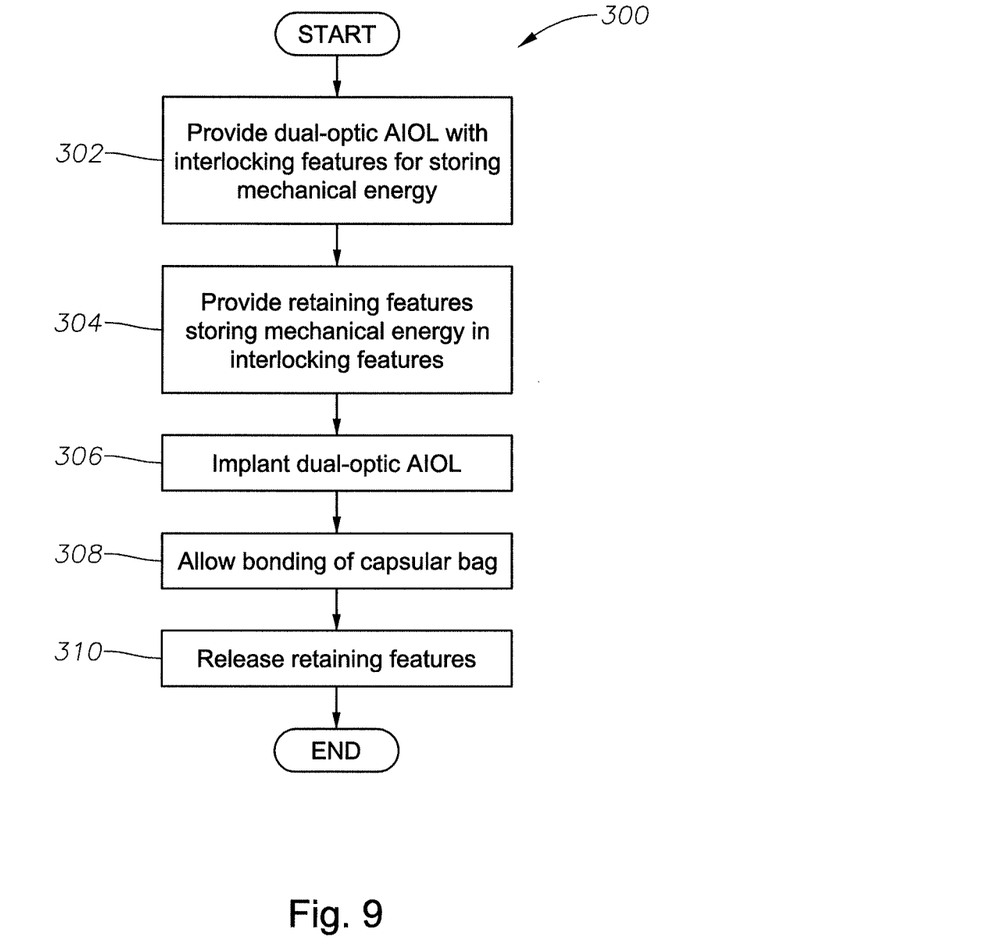
FIG. 9 is a flowchart showing an example method of implanting a dual-optic AIOL according to particular embodiments of the present invention.

FIG. 9 is a flowchart 300 illustrating an example method for implanting a dual-optic AIOL like the one illustrated in FIG. 7. At step 302, a dual-optic AIOL with interlocking features having surface modifications to promote bonding to the capsular bag is provided. At step 304, retaining features holding the AIOL 200 in a disaccommodated state are provided. At step 306, the AIOL is implanted. At step 308, the capsular bag is allowed to heal and to bond to the AIOL. At step 308, the retaining features are disabled to allow the AIOL 200 to move freely in response to the movement of the capsular bag.

Figure 10:
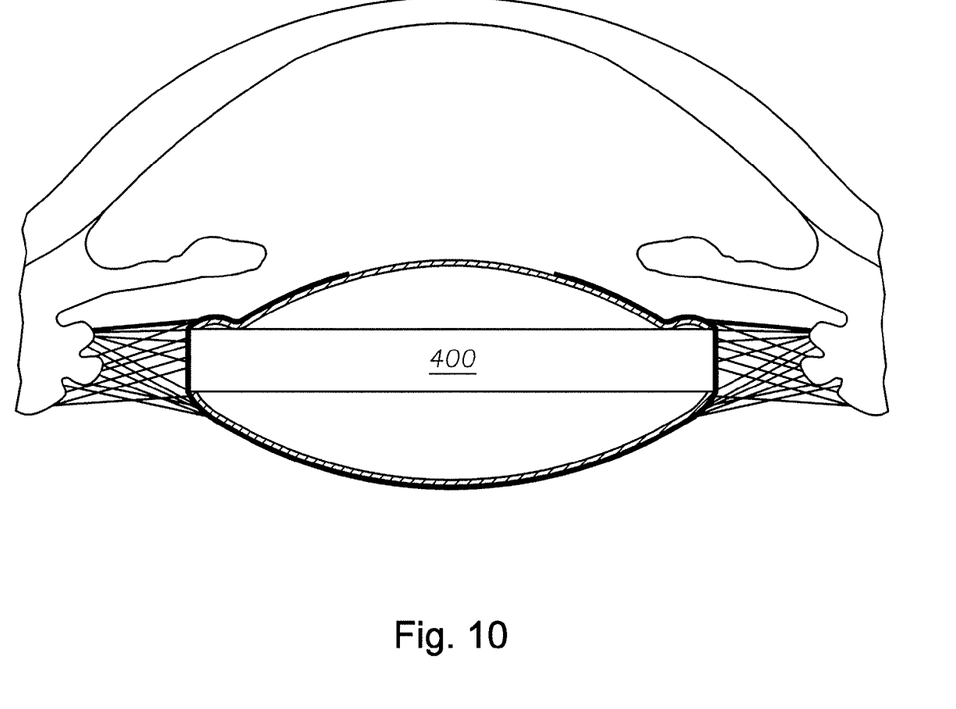
FIG. 10 illustrates a peripheral band usable in conjunction with various embodiments of the present invention.

FIG. 10 illustrates a peripheral band 400 suitable for use with any of the foregoing embodiments described above, although it is illustrated particularly with the lens 10 of FIG. 1. Peripheral band 400 serves to improve the mechanical connection with the capsular bag by preserving the tension in the anterior and posterior zonules as the capsular bag heals around the lens 10. One difficulty that can arise with accommodating IOLs generally is that the AIOL can be somewhat flatter than the natural lens. This causes the more anterior and posterior zonules to be in greater tension as the capsular bag heals around the IOL than they would be around the natural lens. The peripheral band 400 has sufficient width to span the area of the capsular bag where the zonules are attached, thus preventing the capsular bag from flattening in this area and preserving the zonular tension. This advantageously improves the force transfer from the capsular bag. The peripheral band 400 can also be attached to the living hinges 21 illustrated, for example, in FIG. 1, to provide additional leverage for the capsular bag forces to change the shape of the lens 10. The peripheral band 400 can also be made of an elastic material that is mechanically biased toward the accommodated state, allowing the lens 10 to more easily restore to an accommodated position when tension in the capsular bag is relaxed.

As with other embodiments described above, the peripheral band 400 has surface modifications that promote bonding of the capsular bag to the peripheral band 400. The peripheral band 400 is mechanically connected to lens 10 or to the interlocking features 206 of dual-optic AIOL 200 so as to preserve a robust mechanical connection between the capsular bag and the movement of the AIOL. This mechanical connection can be made, for example, by sizing the peripheral band 400 so that it fits snugly around the AIOL, by adhering the peripheral band 400 to the AIOL using adhesive, or by co-polymerizing or otherwise integrally forming the peripheral band 400 with the AIOL. The peripheral band 400 can also include a sharp corner for prevention of PCO.

Various embodiments of the present invention, including examples of AIOLs that promote bonding to the capsular bag and facilitate mechanical response of the AIOL to changes in the capsular bag in order to produce accommodation, have been provided. This description is given for purposes of illustration and explanation. It will be apparent to those skilled in the relevant art that changes and modifications may be made to the invention described above without departing from the scope of the invention as claimed. Such modifications include, for example, the adaptation of any of the described embodiments for drug delivery or the modifications of such features as the peripheral band to reduce positive or negative dysphotopsia.

What is claimed is:

1. An accommodating intraocular lens (AIOL) adapted for implantation into a capsular bag, comprising:
   an outer shell comprising an anterior segment and a posterior segment connected at a living hinge at a periphery of the AIOL, the anterior segment and posterior segment defining an internal void that is fillable with a fill material such that a portion of a periphery of the outer shell expands to directly contact a capsular bag, the outer shell including at least one surface modification at a contact region on at least the portion of the periphery of the outer shell, the surface modification configured to promote growth and adhesion of epithelial cells such that the capsular bag is adhered to the outer shell at the contact region, wherein the outer shell is adapted such that the capsular bag exerts force on the outer shell at the contact region when adhered to the outer shell;

a fill material;

a valve configured to permit injection of the fill material;

at least one sharp peripheral edge shaped to hold the capsular bag to reduce posterior capsule opacification; and a force transfer assembly comprising at least one stiffening rib, the at least one stiffening rib comprising a region of the anterior segment of the outer shell having a greater thickness than adjacent regions of the anterior segment of the outer shell and extending into the internal void only a portion of the way between the anterior segment and the posterior segment, the force transfer assembly adapted to transfer the forces from the capsular bag at the contact region to change the shape of the filled outer shell in response to changes in capsular bag shape, wherein the living hinge is configured such that a void is maintained between the living hinge and the capsular bag, wherein the at least one surface modification comprises one or more of nano-texturing, a surface coating, and a biocompatible adhesive.

2. The AIOL of claim 1, wherein the fill material comprises a polymer gel.

3. The AIOL of claim 1, wherein the outer shell further comprises a peripheral band and wherein the at least one surface modification is on the peripheral band.

4. The AIOL of claim 1, wherein the surface coating comprises one or more of complementary proteins, growth factors for the capsular bag, and chitin.

* * * * *